United States Patent [19]

Sato et al.

[11] 4,289,918
[45] Sep. 15, 1981

[54] ARALKYLATION

[75] Inventors: Atsushi Sato, Tokyo; Isoo Shimizu, Yokohama; Masahito Gotoh, Kawasaki, all of Japan

[73] Assignee: Nippon Petrochemical Company, Limited, Japan

[21] Appl. No.: 171,465

[22] Filed: Jul. 23, 1980

[30] Foreign Application Priority Data

Jul. 24, 1979 [JP] Japan ................................ 54-93173

[51] Int. Cl.$^3$ .............................................. C07C 2/72
[52] U.S. Cl. .................................................. 585/422
[58] Field of Search ......................................... 585/422

[56] References Cited

U.S. PATENT DOCUMENTS

| | | | |
|---|---|---|---|
| 2,742,514 | 4/1956 | Schneider | 585/422 |
| 2,759,984 | 8/1956 | Schlatter | 585/422 |
| 3,079,448 | 2/1963 | Jenny | 585/422 |
| 3,282,875 | 11/1966 | Connolly et al. | 526/243 X |
| 3,882,093 | 5/1975 | Cavanaugh et al. | 568/615 X |

FOREIGN PATENT DOCUMENTS

| | | | |
|---|---|---|---|
| 698956 | 12/1964 | Canada | 585/422 |
| 2233705 | 2/1973 | Fed. Rep. of Germany | 585/422 |
| 896864 | 5/1962 | United Kingdom | 585/422 |
| 977322 | 12/1964 | United Kingdom | 585/422 |

Primary Examiner—John Doll
Attorney, Agent, or Firm—Scully, Scott, Murphy & Presser

[57] ABSTRACT

Provided is a method of aralkylating alkylbenzenes by contacting styrene and alkylbenzene at an elevated temperature in the presence of a resinous perfluoro polymer.

8 Claims, No Drawings

ARALKYLATION

BACKGROUND OF THE INVENTION

This invention relates to a method of aralkylating benzene or alkylbenzenes (hereinafter referred to generically as "alkylbenzenes"). More particularly, this invention is concerned with a method of adding aromatic olefins (hereinafter referred to generically as "styrenes") having a double bond in the position conjugated with the benzene ring to alkylbenzenes in high yield in the addition of olefins or mixtures thereof to alkylbenzenes.

The reaction of adding various olefins to alkylbenzenes is known as Friedel-Crafts reaction and as an important reaction from the standpoint of chemical industry. This addition reaction is classified into an alkylation reaction of alkylbenzenes with aliphatic compounds having an olefinic double bond (hereinafter referred to as "aliphatic olefins"), and an aralkylation of styrenes with alkylbenzenes. The term "olefins" is a general term for both aliphatic olefins (including the so-called diolefins) and aromatic olefins (including styrenes). These terms will be used hereinafter.

Alkylated compounds are used as a starting material in the chemical industry, and per se are used as an insulating or lubricating oil. On the other hand, aralkylated compounds, which are superior in heat resistance, compatibility and electrical characteristics, are known as an industrially preferred aromatic synthetic oil suitable for a heat transfer medium, a plasticizer, a reaction solvent and an insulating oil. Because of the difficulty in the manufacturing process, however, there is only a limited number of chemical enterprises which manufacture such aralkylated compounds independently.

Aralkylated compounds, in their basic chemical structure, have the diphenylmethane skeleton in which two benzene rings are bonded to the same carbon atom. Consequently, unlike alkylnaphthalenes and alkylbiphenyls which have been known as high-boiling aromatic synthetic oils, aralkylated compounds are characteristic in that they are a non-condensed polycyclic aromatic synthetic oil.

Known as the method of obtaining aralkylated compounds is one in which an aralkylation reaction is carried out using halogenated alkylbenzenes with the α-position of alkyl group substituted by a halogen atom and in the presence of a halogenated metallic catalyst such as aluminum chloride, and one in which an aralkylation reaction is carried out using styrenes and in the presence of an acid catalyst. When consideration is given as to whether it is easy or not to treat the by-produced hydrogen halide and to obtain an aralkylating agent α-halogenated alkylbenzenes, the latter method of aralkylation using styrenes in the presence of an acid catalyst is preferred.

As the aralkylation method using styrenes heretofore disclosed there are known the method using a sulfuric acid catalyst shown in British Pat. No. 977,322 and the method using a solid acid catalyst shown in British Pat. No. 896,864.

It goes without saying that, among these catalysts, it is solid acid catalysts that can be used preferably in practical application because of their easiness of separation or removal of catalysts after reaction.

Among solid acid catalysts, moreover, we have found that acidic ion-exchange resins exhibit an activity in the aralkylation reaction.

However, conventional acidic ion-exchange resins, in which a sulfonated styrene-divinylbenzene copolymer is a backbone polymer, are low in aralkylation activity and are further disadvantageous in that, if the reaction temperature is raised with the object of attaining a sufficient activity, the catalyst particles will be destroyed and the acid component will flow out, resulting in the catalyst life being shortened and in the necessity of neutralizing the acid component which has flowed out into the reaction solution.

In the aralkylation reaction using such conventional acidic ion-exchange resins, moreover, there are easily produced dimers or polymers of styrenes because styrenes, particularly styrene, have a much higher polymerization activity than aliphatic olefins such as ethylene and propylene. Also from this point conventional acidic ion-exchange resins have not been preferable.

It is an object of this invention to eliminate the above-mentioned drawbacks associated with the prior art aralkylation.

It is another object of this invention to provide a method of aralkylating alkylbenzenes with less formation of by-products and in high selectivity.

It is a further object of this invention to provide a new aralkylation catalyst of high activity superior in stability and durability.

Other objects of this invention will become clear from the following description.

The aforesaid objects of this invention can be attained by contacting an aromatic olefin having an olefinic double bond conjugated with the benzene ring, with benzene or an alkylbenzene containing alkyl group(s) with a total number of carbon atom of the alkyl group(s) ranging from 1 to 18, at a temperature of 50° to 230° C. and in the presence of a perfluoro polymer having as a repeating unit at least one unit selected from units represented by the general formulae

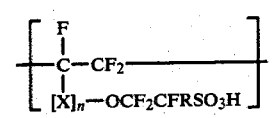

and

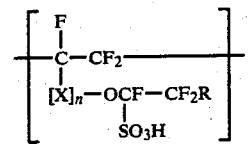

where, n is an integer of 0, 1, or 2,

R is a fluorine atom or a perfluoroalkyl group of $C_1$ to $C_{10}$,

X is $-O(CF_2)_m-$ wherein m is an integer of 1 to 10, $-OCF_2CFY-$, or $-OCFYCF_2-$, and Y is a fluorine atom or trifluoromethyl group.

The aralkylation catalyst used in the method of this invention is a solid, resinous high polymer.

The said catalyst is a perfluoro resinous high polymer (hereinafter referred to as the "resin catalyst") having an acid strength of 0.01 to 5 milliequivalent/g.

Such resin catalyst is characterized by being a polymer having a repeating unit represented by the following general formula (I) or (II):

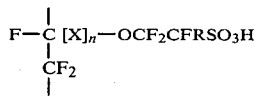
(I)

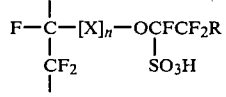
(II)

where, n is an integer of 0, 1, or 2,

R is a fluorine atom or a perfluoroalkyl of $C_1$ to $C_{10}$,

X is $-O(CF_2)_m-$ wherein m is an integer of 1 to 10, $-OCF_2CFY-$, or $-OCFYCF_2-$, and Y is a fluorine atom or trifluoromethyl group.

DESCRIPTION OF THE INVENTION

As is disclosed in U.S. Pat. Nos. 3,282,875 and 3,882,093, the foregoing resin catalyst can be prepared by the polymerization of vinyl compounds represented by the following general formula (III) or (IV):

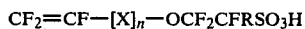
(III)

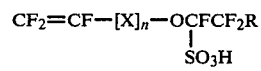
(IV)

where, n, X and R have the same meaning as defined in the foregoing formulae (I) and (II).

Perfluoro vinyl ethers represented by the general formula (III) or (IV) can be polymerized or copolymerized in a perfluoro hydrocarbon solvent in the presence of a perfluoro radical initiator. In some particular polymerization reaction conditions the above vinyl ethers are held in liquid phase, so in this case it is also possible to effect a bulk polymerization without using a solvent. The polymerization temperature, which differs depending on the initiator used, is usually in the range of from $-50°$ C. to $200°$ C. The polymerization pressure, which usually does not constitute a critical condition, depends on the amount of a gaseous comonomer used as a copolymerization monomer. As to the perfluoro hydrocarbon used as a polymerization solvent, perfluoroparaffin or perfluoronaphthene is used preferably. As the polymerization initiator, perfluoro organic peroxides or nitrogen fluorides are preferred. Furthermore, the foregoing perfluoro vinyl ethers can be subjected to emulsion polymerization by radical polymerization or redox polymerization using water as a solvent.

The resin catalyst used in the invention is also obtainable by copolymerizing a perfluoro vinyl ether represented by the foregoing formula (III) or (IV) with perfluoroethylene or perfluoro-α-olefin. The above resin catalyst obtained by the copolymerization of perfluoroethylene and perfluoro vinyl ether is represented by the following general formula (V):

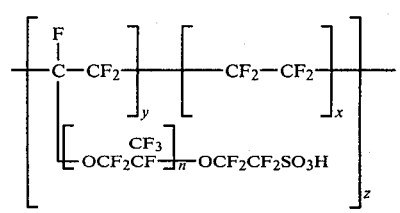
(V)

where, n=0, 1, or 2 x, y and z are integers having next relations x/y=2 to 20 z=500 to 10000

The above copolymer is available under the trade name of "NAFION" resin manufactured by E. I. du Pont Company. The "NAFION" resin, the details of which are set forth in "Du Pont Innovation Vol. 4, No. 3, Spring 1973," now attracts attention for its industrial utilization as a solid super acid[*1].

[*1] Org. Chem., Vol. 42, No. 26, 4187 (1977)
ibid., Vol. 43, No. 26, 4628 (1978)
G. A. Olah, "Friedel-Crafts Chemistry," P367, John Wiley & Sons (1973)

In the method of this invention, the amount of catalyst to be used may be the so-called catalytic amount; usually and preferably it is not smaller than 0.1 milliequivalent based on one mole of alkylbenzenes, one of the reactants. Increase in the catalyst concentration would not change the yield in the aralkylation according to the method of the invention, but in order to shorten the reaction time and to carry out the reaction efficiently a catalyst amount not smaller than 1 milliequivalent is preferable in practical use.

The reaction temperature is preferably in the range of from 50° to 230° C. Reaction temperatures lower than 50° C. are not preferred because styrenes will polymerize resulting in the yield of the object aralkylated compounds being decreased. Reaction temperatures higher than 230° C. are not preferred, either, because the dealkylation and isomerization of alkylbenzenes will become marked, and besides, the decomposition of the resin catalyst will begin to take place. More preferred reaction temperature are from 60° C. to 220° C. In the method of this invention, the reaction temperature can be suitably chosen within the range not lower than 50° C. and not higher than 230° C., but alkylbenzenes and styrenes must be held in liquid phase. The reaction pressure, which inevitably varies according to the kind of alkylbenzenes and styrenes fed to the reaction, can be suitably chosen within a range of pressure sufficient to hold the starting materials in liquid phase. Usually, a pressure not higher than 50 kg/cm²·G is sufficient.

The object products in the method of this invention are 1:1 adducts with one molecule of styrenes added to one molecule of alkylbenzenes, and 1:2 adducts with two molecules of styrenes added to one molecule of alkylbenzenes. As explanation is here given about 1:1 and 1:2 adducts in the case of using xylene and styrene as starting materials as an example. The 1:1 adduct is a monostyrenated xylene (1-xylyl-1-phenylethane), but in the case of using a mixed xylene as a starting material it can be a mixture of four kinds of isomers according to the constituent, four kinds of xylene isomers. The 1:1 adduct exhibits a single peak of 210 in the molecular weight determination according to mass analysis (hereinafter referred to as "m/e value"), and it is a liquid having a boiling point at atmospheric pressure ranging from 292° to 305° C. The 1:2 adduct, which is a compound with two mols of styrene added to xylene, exhibits a single peak of 314 m/e value, but in the case of using a mixed xylene as a starting material it can be a mixture of multiple kind isomers according to the constituent, four kinds of xylene isomers or according to the change in position to which styrene is added. The 1:2 adduct has a boiling point ranging from 180° to 240° C. under a reduced pressure of 3 mmHg. Heavier products, which are polymerizates of styrene, are not desirable so the formation thereof should be avoided.

According to the method of this invention, the foregoing 1:1 and 1:2 adducts can be obtained in high yield with less formation of styrene dimer and heavier products.

The alkylbenzenes used in the method of this invention are benzene or alkylbenzenes with a total number of carbon atom of the alkyl group(s) being 1 to 18. Alkylbenzenes with a total number of carbon atoms of the alkyl group(s) being 19 or more are not preferred because there will occur dealkylation and isomerization resulting in that aralkylated alkylbenzenes, the object compounds of this invention, cannot be obtained in high yield. The alkyl group includes straight chain, branched, and cyclic side chain alkyls such as indane and tetralin. Examples of alkylbenzenes, though they do not restrict the invention, are lower alkylbenzenes such as benzene, toluene, o-, m- or p-xylene, ethylbenzene, 1,2,3-, 1,2,4-, or 1,3,5-trimethylbenzene, o-, m- or p-ethyltoluene, propylbenzene, and cumene; higher alkylbenzenes with a total number of carbon atoms of the alkyl group(s) being 4 to 18; and alkylbenzenes, alkyl group of which is a fused cyclic alkyl side chain, such as indane and tetralin. In the practice of this invention, these alkylbenzenes may be used alone or as a mixture of two or more. Also, distillates incorporating aliphatic hydrocarbons may be used in working the invention on condition that they contain the aforementioned alkylbenzenes.

Among the aromatic olefins, one starting material used in the invention, it is those compounds (styrenes) having a double bond in the position conjugated with the benzene ring that make the aralkylation of the invention possible, examples of which are styrene, alkyl-substituted styrenes such as α-methylstyrene, β-methylstyrene and vinyltoluene, aromatic diolefins such as divinylbenzene, further alkylbenzenes, alkyl group of which is a fused cyclic side chain having double bond(s) conjugated with the benzene ring, such as indene and alkylindenes. In working the method of the invention these styrenes may be used alone or as a mixture of two or more.

Furthermore, as a starting material which may be used preferably in the method of this invention, mention may be made of a distillate rich in aromatics (hereinafter referred to as the "aromatic by-product oil") having a boiling range of 65° to 198° C. among the cracked oils by-produced from thermal cracking at a temperature above 700° C. of petroleum hydrocarbons for the manufacture of ethylene. The aromatic by-product oil, whose composition varies according to the kind of the starting oil fed to the cracking apparatus and also according to the conditions for the cracking reaction, is a mixture of hydrocarbons having 5 to 10 carbon atoms varying in the range of saturated aliphatic hydrocarbons 5 to 15% by weight, aromatics as alkylbenzenes 35 to 85% by weight, aliphatic olefins 2 to 10% by weight, and styrenes 2 to 15% by weight. Thermal cracked by-product oils having a boiling point higher than 198° C. are not preferred because they contain naphthalene and other condensed polycyclic aromatics. Because of containing dienes such as cyclopentadienes which easily polymerize, a distillate having a boiling point lower than 65° C. is not preferred. Table 1 below entitled "Composition of the aromatic by-product oil" shows an example of analysis of the aromatic by-product oil.

TABLE 1

| | Composition of the aromatic by-product oil | | | |
|---|---|---|---|---|
| | Saturated aliphatic hydrocarbons | Alkyl-benzenes | Aliphatic olefins | Styrenes | Total |
| $C_5$ | 4.2 | — | 3.9 | — | 8.1 |
| $C_6$ | 7.3 | 33.4 | 4.7 | — | 45.4 |
| $C_7$ | 1.1 | 19.9 | 0.9 | — | 21.9 |
| $C_8$ | 0.7 | 10.5 | 0.6 | 4.9 | 16.7 |
| $C_9$ | 0.3 | 4.4 | 0.2 | 2.3 | 7.2 |
| $C_{10}$ | 0.1 | 0.3 | 0.1 | 0.2 | 0.7 |
| Total | 13.7 | 68.5 | 10.4 | 7.4 | 100.0 |

(The numerical values are percentages by weight)

If the aromatic by-product oil is used as the starting material in the aralkylation according to the method of this invention, there can be obtained aralkylated compounds having superior characteristics in practical use and being suitable for use as a heat transfer medium, a plasticizer, various solvents and insulating oils.

Regardless of the above gist of the invention, independently isolated styrenes not containing aliphatic olefins, for example styrene and/or α-methylstyrene, may be used in working the method of the invention, and this should be understood to be a working of the invention inevitably.

In this invention, the reaction mol ratio, namely the molar ratio of alkylbenzenes to styrenes, is a maximum of 1:2, within which range the amount of styrenes to be used is chosen suitably. In this range the production ratio of the object products can be varied from 1:0.91 to 1:0.01 in terms of 1:1 adduct to 1:2 adduct ratio. Using excess styrenes beyond this molar ratio of 1:2 is not desirable because the conversion of styrenes into the object products would be decreased and polymerizates of styrenes would be increased.

The process may be carried out either as a batch or continuous type of operation. It has been generally established that the more intimate the contact between the feedstock and the catalyst, the better the yield of desired product obtained. With this in mind, the present process, when operated as a batch operation, is characterized by the use of vigorous mechanical stirring or shaking of the reactant and catalyst.

When employing a continuous process, the feed streams may be contacted with the catalyst in any suitable reactor. In one embodiment, the catalyst is packed in a vertical, tubular reactor bed. The flow of the reactant feed stream may be upflow or downflow.

Working and comparative examples are given below to illustrate the invention more concretely.

EXAMPLES 1–3

(Reaction of orthoxylene and styrene)

Into a reaction vessel equipped with a stirrer, a reflux condenser, a thermometer and a dropping funnel were charged 530 g. of orthoxylene and a predetermined amount of a resin catalyst ("Nafion" Powder 501).

The resin catalyst used had been converted from K+ type to H+ type by sulfuric acid treatment.

Then the temperature was raised to 140° C., and 104 g. of styrene was added dropwise over a 1 hour period with stirring. Thereafter, the stirring was continued for additional 30 minutes and then the reaction was brought to an end.

After cooling, the resin catalyst was filtered off and a distillate distilling at a temperature of 125° to 140° C. was obtained by distillation under a reduced pressure of 3 mmHg.

The distillates thus obtained all exhibited a single peak of 210 m/e value as a result of mass analysis and they were a 1:1 adduct of styrene and orthoxylene. The results are set out in Table 1 below.

The "styrene yield" as referred to in the same table is a numerical value expressed in terms of a mol% of the ratio of styrene converted to the object 1:1 adduct to the styrene fed to the reaction.

TABLE 1

| Example | Catalyst amount(gr) | Distillate yield(gr) | Styrene yield(5) | Acid value of reaction solution after filtration (mgKCH/gr) |
|---|---|---|---|---|
| 1 | 5 | 170 | 81 | 0.01 |
| 2 | 12 | 190 | 90 | 0.01 |
| 3 | 20 | 200 | 95 | 0.01 |

EXAMPLES 4–6

Into a reaction vessel having a capacity of 1 liter and equipped with a stirrer, a reflux condenser, a thermometer and a dropping funnel were charged a predetermined amount of an alkylbenzene and 15 g. of the same resin catalyst as that used in Example 1, and the temperature was raised up to the reaction temperature. Then styrenes were added dropwise over a 1 hour period with stirring. Thereafter, the stirring was continued for additional 30 minutes and then the reaction was brought to an end. After cooling, the resin catalyst was filtered off and aralkylated distillates were obtained by distillation under reduced pressure. The results are set out in Table 2 below.

TABLE 2

| | Alkyl-benzenes (gr) | Styrenes (gr) | Reaction temp.(°C.) | Styrene yield(%) | Acid value of reaction solution (mgKOH/gr) |
|---|---|---|---|---|---|
| Ex. 4 | m-xylene 530 | α-methyl styrene 128 | 70 | 80 | 0.00 |
| Ex. 5 | 1,2,4-trimethyl 544 | Styrene 104 | 170 | 92 | 0.01 |
| Ex. 6 | Tetralin 670 | m.p-vinyl toluene 128 | 210 | 90 | 0.02 |

Comparative Example 1

Reaction of styrene and orthoxylene was carried out in the same manner as in Example 2 except that there were used as catalysts Amberlist 15 and Amberlite IR-120 (both manufactured by Organo Co.), sulfonated products of styrene-divinylbenzene copolymer.

After completion of the reaction, the catalysts were filtered off and then the acid number of the reaction solution was determined, the results of which are as shown below.

| Catalyst | Acid value (mg/KOH/gr) |
|---|---|
| Amberlist 15 | 2.7 |
| Amberlite IR-120 | 3.8 |

With these conventional ion-exchange resins, a considerable efflux of acid component in the resins was recognized, so it was necessary to neutralize the acid efflux.

Comparative Example 2

Reaction was carried out in the same manner as in Example 4 except that Amberlist 15 (20 g.) was used as catalyst. But the styrene yield was only 8% and the conversion was extremely low.

EXAMPLE 7

The aromatic by-product oil as shown in the foregoing Table 1 as exemplar analytical data, was used in this example. A mixture of 100 g. of toluene and 10 g. of the same resin catalyst as that used in Example 1 was heated with stirring and maintained at a temperature of 105° C. Then, 1000 g. of the aromatic by-product oil was added dropwise to the above mixture in 3 hours. After the dropping, the reaction was further continued for 30 minutes at 105° C. with stirring, and after the reaction, the catalyst was filtered off from the reaction product. Then, 960 g. of a light fraction up to the distilling temperature of 225° C. was removed by atmospheric pressure distillation. Further, the remainder was subjected to reduced pressure distillation at 3 mmHg and 110 g. of a first fraction of 135°–170° C. in distilling temperature, and 25 g. of a second fraction of 190°–240° C. were obtained.

The first fraction was a mixture giving the m/e peak distribution of 182, 196, 210, 224, 238 and 242. All the components of this fraction were diphenylmethane type compounds ($C_nH_{2n-14}$). The second fraction was a mixture giving the m/e peak distribution of 286, 300, 314 and 328 and was composed of triphenylmethane type compounds ($C_nH_{2n-22}$). In the above test results, the reaction products of $C_nH_{2n-6}$ as the adducts of aliphatic olefins were not observed.

We claim:

1. Method of aralkylating benzene or alkylbenzenes, which method comprises contacting an aromatic olefin having an olefinic double bond conjugated with the benzene ring, with at least one compound selected from benzene and alkylbenzenes containing alkyl group or groups with a total number of carbon atom of the alkyl group or groups ranging from 1 to 18, at a temperature of 50° to 230° C. and in the presence of a perfluoro polymer having at least one repeating unit selected from the units represented by the general formulae

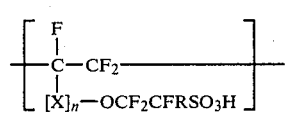   (I)

and

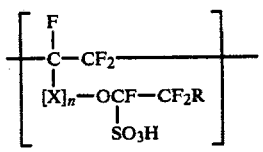
(II)

where,
n is an integer of 0, 1, or 2,
R is a fluorine atom or a perfluoroalkyl group of $C_1$ to $C_{10}$,
X is $-O(CF_2)_m-$ wherein m is an integer of 1 to 10, $-OCF_2CFY-$, or $-OCFYCF_2-$, and
Y is a fluorine atom or trifluoromethyl group.

2. The method as defined in claim 1, in which the aromatic olefin is at least one compound selected from the group consisting of styrene, α-methylstyrene, β-methylstyrene, and vinyltoluene.

3. The method as defined in claim 1, in which the alkylbenzene is an alkylbenzene with a total number of carbon atom of the alkyl group or groups ranging from 1 to 4.

4. The method as defined in claim 1 or claim 3, in which the alkylbenzene is at least one compound selected from the group consisting of toluene, xylene, ethylbenzene, triethylbenzene, ethyltoluene, propylbenzene, and cumene.

5. The method as defined in claim 1, in which benzene or alkylbenzenes contained in a distillate having a boiling range of 65° to 198° C. among the cracked oils by-produced from cracking of petroleum hydrocarbons at a temperature above 700° C. are contacted with aromatic olefins contained in said distillate.

6. The method as defined in claim 1 or claim 5, in which the perfluoro polymer consists essentially of the repeating unit represented by the formula $-(CF_2-CF_2)-$ and at least one repeating unit selected from the units represented by the general formulae (I) and (II).

7. The method as defined in claim 6, in which the perfluoro polymer has a repeating unit represented by the general formula

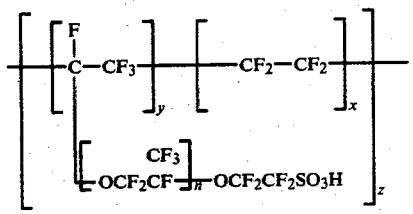

where, n is as defined above, x, y and z are integers, respectively, x/y=2 to 20, and z=500 to 10,000.

8. The method as defined in claim 7, in which the amount of the perfluoro polymer used is 0.1 milliequivalent/gr or more based on the amount of at least one compound selected from benzene and alkylbenzenes.

* * * * *